(12) United States Patent
Sangster et al.

(10) Patent No.: US 11,345,113 B2
(45) Date of Patent: May 31, 2022

(54) COMPOSITE PROTECTIVE SHEET MATERIAL

(71) Applicant: Cerium Group Limited, London (GB)

(72) Inventors: Clive L. Sangster, East Sussex (GB); Timothy Noakes, Kent (GB)

(73) Assignee: Cerium Group Limited, London (GB)

( * ) Notice: Subject to any disclaimer, the term of this patent is extended or adjusted under 35 U.S.C. 154(b) by 493 days.

(21) Appl. No.: 15/814,587

(22) Filed: Nov. 16, 2017

(65) Prior Publication Data

US 2018/0072015 A1   Mar. 15, 2018

Related U.S. Application Data

(63) Continuation of application No. 13/542,748, filed on Jul. 6, 2012, now abandoned.

(30) Foreign Application Priority Data

Aug. 30, 2011 (GB) ..................................... 1114991

(51) Int. Cl.
*B32B 3/06* (2006.01)
*B32B 7/12* (2006.01)
(Continued)

(52) U.S. Cl.
CPC .................. *B32B 3/06* (2013.01); *B32B 7/12* (2013.01); *B32B 27/306* (2013.01); *B32B 27/32* (2013.01); *A45C 11/04* (2013.01); *A61K 9/02* (2013.01); *A61K 9/025* (2013.01); *B32B 3/02* (2013.01); *B32B 7/05* (2019.01); *B32B 37/0076* (2013.01); *B32B 2307/748* (2013.01); *B32B 2405/00* (2013.01); *B32B 2551/00* (2013.01); *B65G 49/069* (2013.01); *G02C 7/16* (2013.01);
(Continued)

(58) Field of Classification Search
None
See application file for complete search history.

(56) References Cited

U.S. PATENT DOCUMENTS 2,348,220 A * 5/1944 Kline .......................... C09J 7/21
428/355 EN
2,399,545 A   4/1946 Davis
(Continued)

FOREIGN PATENT DOCUMENTS

DE   20 2004 012108    12/2005
EP      1 160 176       12/2001
(Continued)

OTHER PUBLICATIONS

Definition "Lens" from Merriam-Webster online dictionary, retrieved Apr. 24, 2016.

*Primary Examiner* — Linda L Gray
(74) *Attorney, Agent, or Firm* — Clark & Brody LP

(57) ABSTRACT

A composite protective sheet material for covering a smooth surface of a transparent material, especially but not exclusively for covering the surface of a lens. It comprises a film substrate at least one main surface of which is covered by an adhesive coating. At least a part of the said at least one main surface of the substrate is free or substantially free of adhesive, or has less adhesive applied to it than does the rest of that surface, thereby to provide a finger lift region of the film at an edge of the surface covered thereby.

10 Claims, 5 Drawing Sheets

(51) Int. Cl.
*B32B 27/32* (2006.01)
*A61K 9/02* (2006.01)
*G02C 9/04* (2006.01)
*G02C 7/16* (2006.01)
*A45C 11/04* (2006.01)
*B32B 37/00* (2006.01)
*B32B 3/02* (2006.01)
*B32B 7/05* (2019.01)
*B65G 49/00* (2006.01)
*B32B 27/30* (2006.01)
*B65G 49/06* (2006.01)

(52) U.S. Cl.
CPC ........... *G02C 9/04* (2013.01); *Y10T 156/1062* (2015.01); *Y10T 428/24612* (2015.01)

(56) References Cited

U.S. PATENT DOCUMENTS

| | | | |
|---|---|---|---|
| 2,510,120 A | 6/1950 | Leander | |
| 2,759,394 A | 8/1956 | Evans | |
| 3,193,431 A * | 7/1965 | Seifert | B65C 3/12 156/351 |
| 3,648,835 A | 3/1972 | Yucel | |
| 4,076,373 A | 2/1978 | Moretti | |
| 4,274,232 A | 6/1981 | Wylde | |
| 4,288,485 A * | 9/1981 | Suominen | A47H 23/00 156/193 |
| H377 H | 12/1987 | Greig | |
| 4,716,601 A * | 1/1988 | McNeal | A61F 9/025 2/434 |
| 4,793,002 A | 12/1988 | Simon | |
| 5,082,439 A * | 1/1992 | Kaminski | B29C 49/2408 156/DIG. 31 |
| H1023 H | 3/1992 | Wiseman | |
| 5,191,897 A | 3/1993 | Meshel | |
| 5,212,011 A | 5/1993 | Ishikawa et al. | |
| 5,343,657 A | 9/1994 | Ohlin, Jr. | |
| 5,374,482 A | 12/1994 | Ozari et al. | |
| 5,502,516 A | 3/1996 | Elterman | |
| 5,667,858 A | 9/1997 | Pokorny | |
| 5,820,958 A | 10/1998 | Swallow | |
| 6,149,750 A | 11/2000 | Parish et al. | |
| 6,177,032 B1 | 1/2001 | Smith | |
| 6,333,073 B1 | 12/2001 | Nelson et al. | |
| 6,458,440 B1 * | 10/2002 | Merritt | B65D 57/00 206/448 |
| 6,557,995 B1 | 5/2003 | Edwards | |
| 7,036,929 B1 | 5/2006 | Harvey | |
| 2001/0035936 A1 | 11/2001 | Maisnik | |
| 2004/0241387 A1 | 12/2004 | Lian | |
| 2006/0182956 A1 | 8/2006 | Kamiya | |
| 2007/0248817 A1 | 10/2007 | Sieber et al. | |
| 2010/0045925 A1 | 2/2010 | Trujillo | |
| 2011/0181828 A1 * | 7/2011 | Yi | G02B 30/34 351/47 |
| 2012/0137414 A1 | 6/2012 | Saylor | |
| 2012/0295054 A1 | 11/2012 | Hope | |

FOREIGN PATENT DOCUMENTS

| | | | |
|---|---|---|---|
| EP | 2 204 259 | 7/2010 | |
| EP | 2565026 | 3/2013 | |
| GB | 2 039 810 | 8/1980 | |
| WO | 03/042312 | 5/2003 | |
| WO | WO2011019198 * | 2/2011 | B44C 3/02 |

* cited by examiner

COMPOSITE PROTECTIVE SHEET MATERIAL

The present invention relates to a composite protective sheet material for covering a smooth surface of a transparent material, especially but not exclusively for covering the surface of a lens, comprising a film substrate and an adhesive coating which covers at least one main surface of the film substrate.

Such a sheet material is applied to such a smooth surface to cover it and thereby protect it from scratches or other damage prior to use.

A disadvantage of such a sheet material is that is that it is difficult to peel off when the time comes for the transparent material, whether the latter is in the form of a lens, a window, or the transparent cover of a computer screen, to be put into use, especially if the transparent material is in the form of a lens for use in spectacles which are currently made thin so that their edges are especially thin.

The present invention seeks to provide a remedy.

Accordingly, the present invention is directed to a composite protective sheet material as set out in the opening paragraph of the present specification, characterised in that at least a part of the said at least one main surface of the substrate is free or substantially free of adhesive, or has less adhesive applied to it than does the rest of that surface, thereby to provide a finger lift region of the film at an edge of the surface covered thereby.

The sheet material may be elongate, for example in the form of tape, which may be a roll of tape, which may be wound onto a reel.

The said part may be an elongate strip. If the sheet material is also elongate, the strip may run along the length thereof. If the sheet material is in the form of a tape, the said part may extend all the way along the tape. This provides the advantage that wherever the tape is cut transversely, a finger lift region will be provided. It also provides the advantage of ease of manufacture, for example by securing a short strip of paper or other material around a roller which roller is used to even the spread of adhesive over the film substrate when the composite sheet material is manufactured.

The adhesive may be visually distinct from the film substrate, for example it may be made visually distinct by being coloured with a dye, to render the position of the finger lift region more evident. This is all the more so if the film substrate is transparent or at least translucent.

The present invention extends to a lens having a surface covered by a composite protective sheet material in accordance with the present invention.

An example of a composite protective sheet material made in accordance with the present invention will now be described in greater detail with reference to the accompanying drawing, in which.

Figure 1:
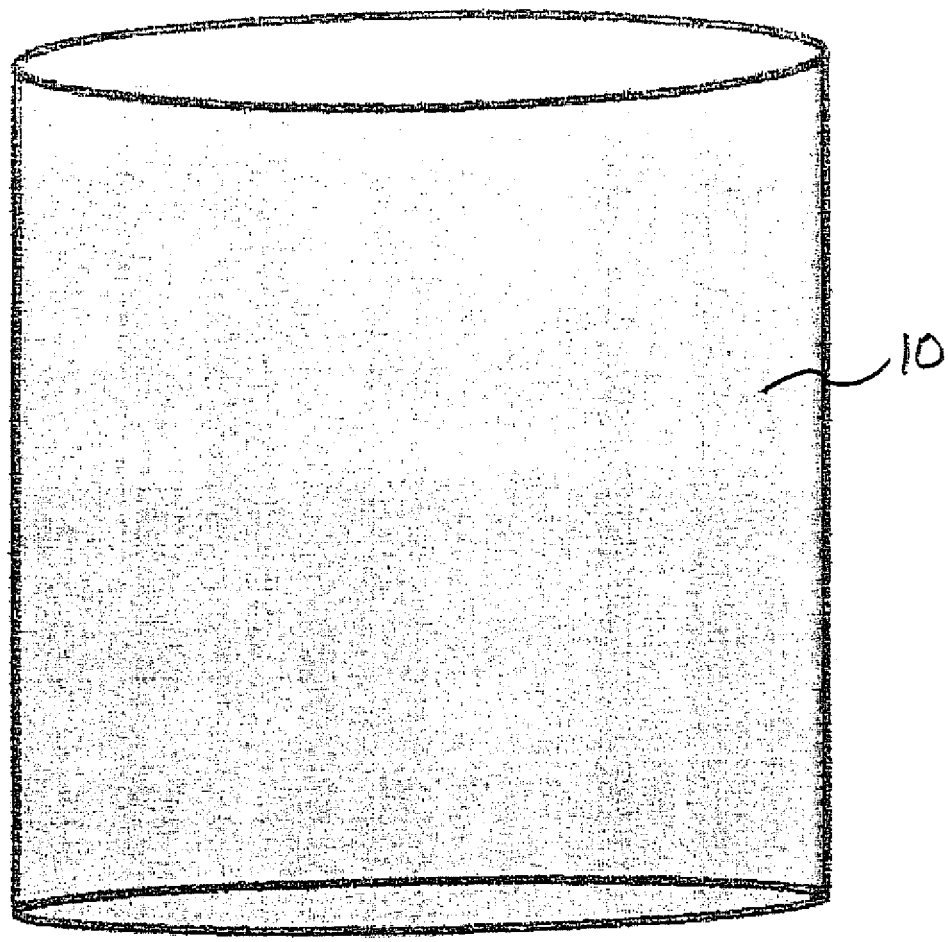
FIG. 1 shows a roll of tape made in accordance with the prior art.
Figure 2:
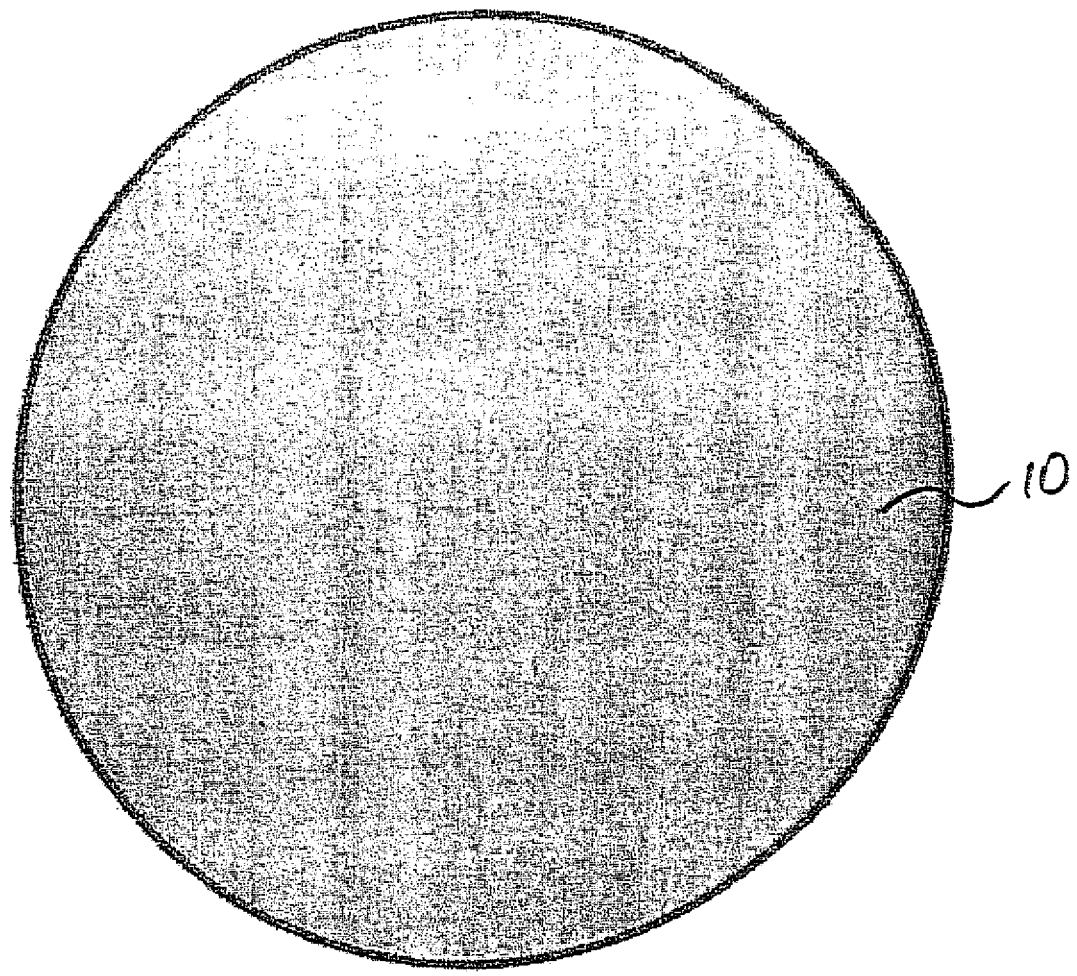
FIG. 2 shows a view from above of a circular lens covered with a portion of the tape cut in the shape of a disc from the roll shown in FIG. 1.

The prior art tape 10 shown in FIGS. 1 and 2 comprises a composite protective sheet material for covering the surface of a lens, comprising a film substrate and an adhesive coating which covers at least one main surface of the film substrate. The adhesive has been applied uniformly over the entire main surface on one side of the tape, and therefore attaches everywhere to that side of the circular lens to which it is secured as shown in FIG. 2.

Figure 3:
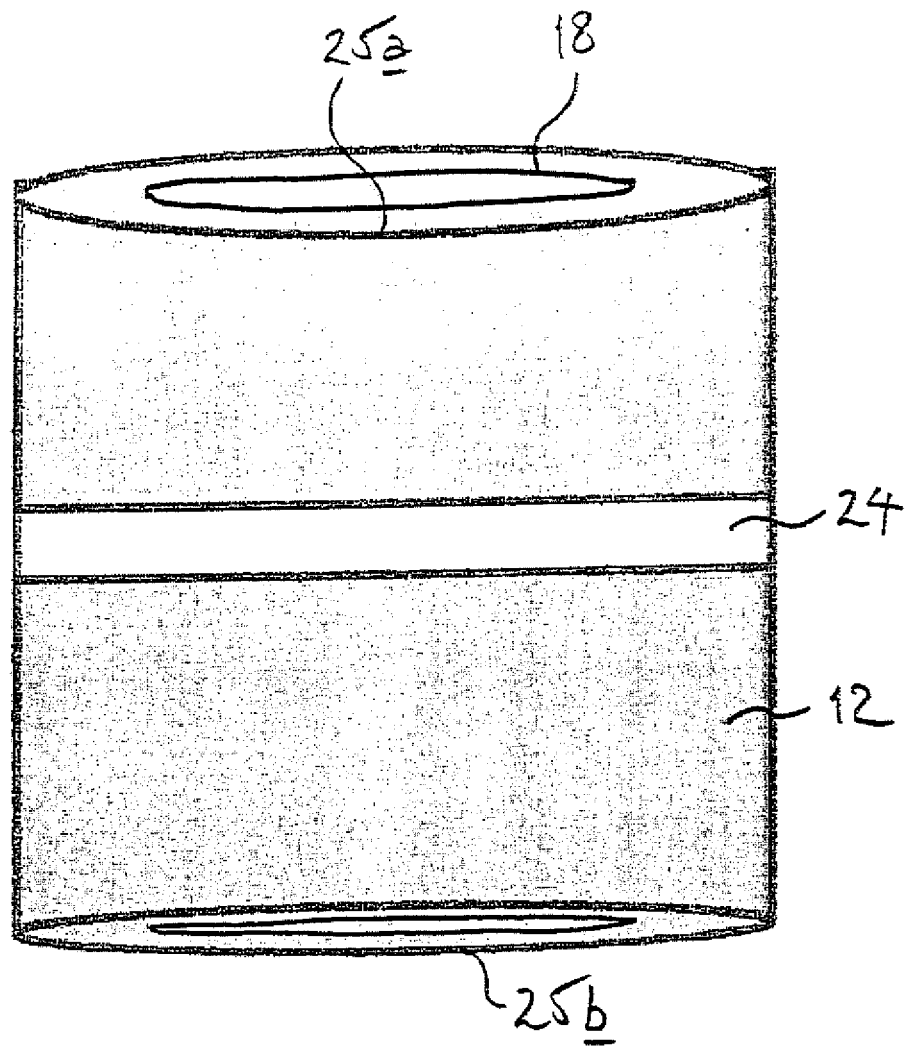
FIG. 3 shows diagrammatically a roll of tape embodying the present invention.
Figure 4:
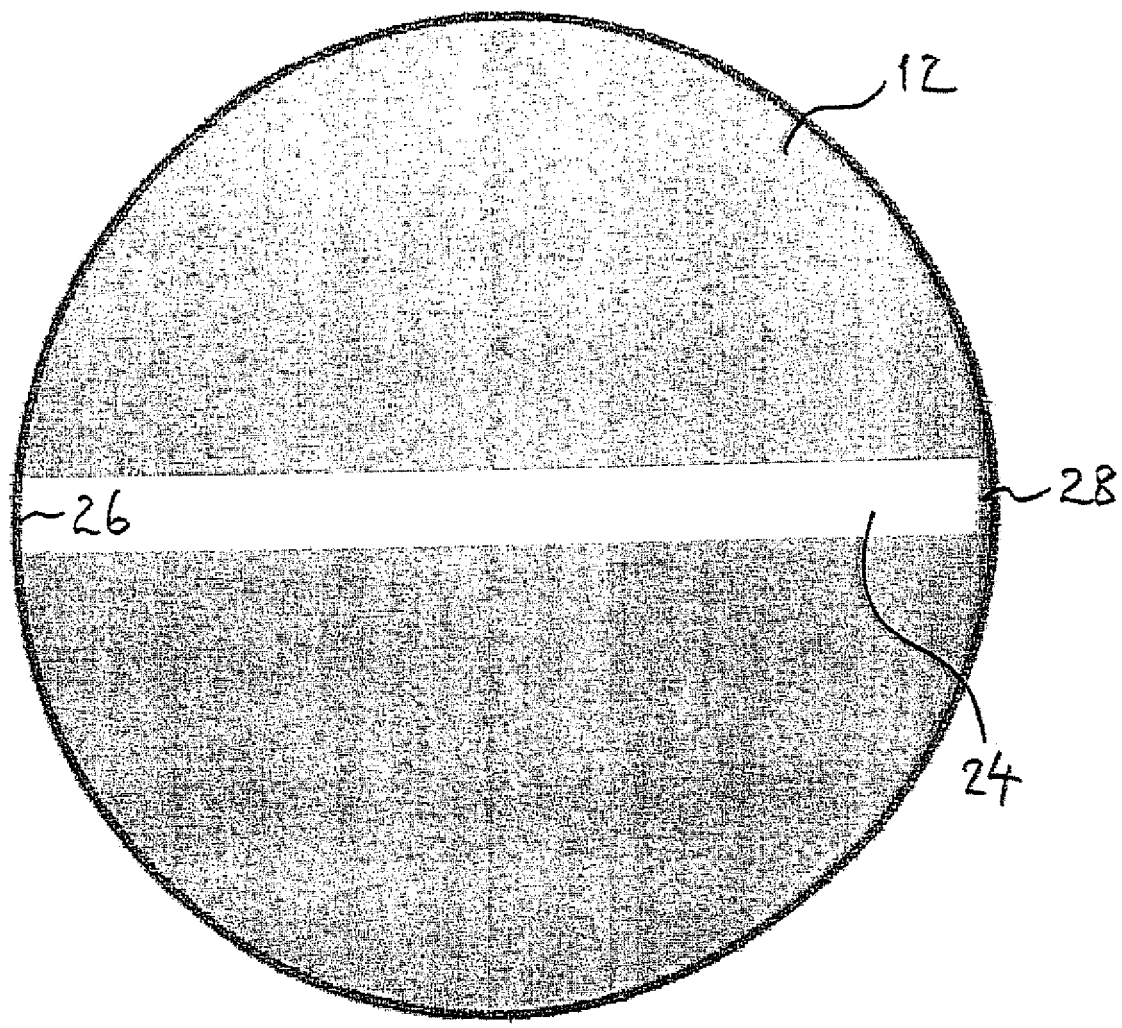
FIG. 4 shows a view from above of a circular lens covered with a portion of the tape cut in the shape of a disc from the roll shown in FIG. 3.
Figure 5:
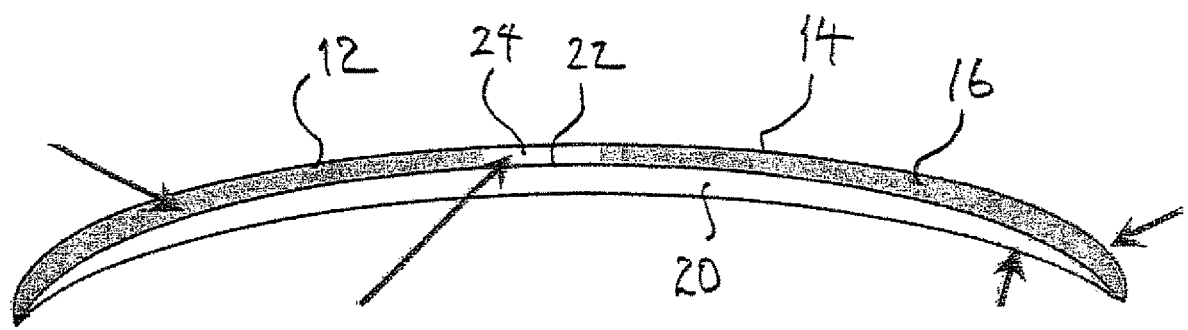
FIG. 5 shows diagrammatically and not to scale a cross-sectional view of the lens and cover shown in FIG. 4 taken in the plane indicated by the line V-V in FIG. 4.

The tape 12 embodying the present invention and shown in FIGS. 3 to 5 comprises a film substrate 14 of substantially uniform thickness of transparent terpolymer polyethylene and an adhesive coating 16 of substantially uniform thickness of an acrylic based copolymer in solution, coloured with a green dye, which covers one main surface of the film substrate 14.

The substrate is substantially 100 mm wide and substantially 100 microns in thickness. The roll of tape in FIG. 3 is about 35 m in length. The coating 16 is substantially 22 microns in thickness.

FIG. 3 shows a roll of the tape 12 wound on a reel 18. In FIGS. 4 and 5, a circular portion of tape 12 from the roll shown in FIG. 3 has been cut to substantially exactly the dimensions of a plastics lens 20 one surface 22 of which the tape 12 covers, to protect that surface 22 against scratching and other possible damage.

However, unlike the prior art tape 10, the tape 12 shown in FIGS. 3 to 5 is formed with an area in the form of a strip 24 running the entire length of the roll shown in FIG. 3 and therefore across the entire width of the circle of tape, as shown in FIG. 4, in which strip there is no adhesive on the film substrate 14. The strip lies substantially midway between the edges 25a and 25b of the tape 12.

As a result, although the lens surface under the strip 24 is covered and therefore protected by the film substrate 14, there is a small void between the lens 20 and the film substrate 14 under this strip 24, which provides finger lift regions 26 and 28 where the strip 20 meets the edge of the lens 20. The position of these regions 26 and 28 is made evident to the user by virtue of the transparency of the film substrate 14 and the fact that the adhesive of the coating 16 is coloured green, so that the strip stands out as more or less colourless against the green of the adhesive. In these regions 26 and 28, because of the absence of adhesive 16, it is easier for the user to insert a fingernail for example to lift the tape 12 and then to peel it off the lens 20 when the lens 20 is to be prepared ready for use.

The strip 24 is substantially 9 mm wide.

Instead of terpolymer polyethylene, the film substrate 14 may be one of poly(ethylene/acid) copolymer, or polyethylene ethyl vinyl acetate, for example, or indeed of any suitable plastics material that will readily occur to those of the art. Instead of an acrylic based copolymer in solution, the adhesive of the coating 16 may be one of a modified acrylic copolymer or a hydrocarbon resin, or indeed any adhesive that will readily occur to the reader of the art as being suitable. The adhesive may be solvent based, water based or hot melt. It may be coloured or otherwise shaded any colour or shade other than green, and it does not have to be coloured or shaded at all although this will assist in showing the finger lift regions.

The width of the tape 12 may vary from 50 mm or less to 200 mm or more. It may have any length beyond about 50 mm. The thickness of the film substrate 14 may be from 100 microns to 130 microns, or it may be from 50 microns, or less, to 200 microns, or more. The thickness of the adhesive coating 16 may be substantially 15 microns, or from 5 microns, or less, to 50 microns, or more.

The width of the strip 24 may be from 7 mm to 10 mm, although it may be narrower or wider, provided it is not so wide that it creates an unacceptable risk of accidental peeling from a lens for example, nor so narrow that it does not afford assistance in enabling the sheet material to be peeled off a lens for example. The strip 24 may be off centre as regards its position across the width of the tape 12, provided it is spaced from the edges thereof. The area in which adhesive is absent or at least thinner does not have to be a strip 24, but may comprise a plurality of circles or other shapes for example spread over the film substrate 14.

The tape 12 may be provided with a releasable peel-off backing (not shown) which covers the adhesive coating 16.

The plastics of the lens 20 may be allyl diglycol carbonate or any other suitable plastics material such as polycarbonate. The material of the lens may instead comprise glass.

Many other modifications and variations to the tape 12 shown in FIGS. 3 to 5 may occur to the reader without taking the resulting construction of tape outside the scope of the present invention.

We claim:

1. A method of protecting a surface of a lens, said surface having a peripheral edge forming a peripheral edge of said lens, dimensions of the peripheral edge of said lens being such that the peripheral edge of the lens forms entire outer boundary of said lens, comprising the following steps:
    (a) coating at least one main surface of a tape with an adhesive, the step of coating including securing a strip of material around a roller and using the roller to spread the adhesive over said at least one main surface of the tape, so as to leave an area of said at least one main surface in which there is no adhesive coating;
    (b) forming a roll of the tape; and
    (c) cutting a portion of the tape from the roll and conforming said portion to substantially the exact dimensions of the peripheral edge of said lens;
    the portion being so cut and the lens being so covered with the cut portion that there is a void between the lens and a portion of said area whereby that portion of said area provides a finger lift region at said edge of said lens.

2. A method according to claim 1, wherein said area is a strip along the length of the tape.

3. A method according to claim 2, wherein the strip is central between main edges of the tape.

4. A method according to claim 2, wherein the strip is off center in regards to its position across a width of the tape.

5. A method according to claim 1, wherein the roll of the tape is formed by rolling the tape onto a reel.

6. A method according to claim 1, wherein the adhesive coating is visually distinct from the tape.

7. A method according to claim 6, wherein the adhesive is coloured with a dye.

8. A method according to claim 7, wherein the tape is translucent.

9. A method according to claim 7, wherein the tape is transparent.

10. A method according to claim 2, wherein a width of said strip is in the range from 7 mm to 10 mm.

* * * * *